US000001407H

United States Statutory Invention Registration [19]

[11] Reg. Number: H1407

Sanderson et al.

[43] Published: Jan. 3, 1995

[54] SYNTHETIC LUBRICANT BASE STOCKS BY CO-REACTION OF VINYLCYCLOHEXENE AND LONG-CHAIN OLEFINS

[75] Inventors: John R. Sanderson, Leander; Wheeler C. Crawford, Houston, both of Tex.

[73] Assignee: Texaco Chemical Company, White Plains, N.Y.

[21] Appl. No.: 580,439

[22] Filed: Sep. 10, 1990

[51] Int. Cl.[6] ..... C10M 107/02; C07C 2/02; C07C 2/56; C08F 132/00

[52] U.S. Cl. ..... 585/10; 585/18; 585/12; 585/502; 585/709; 526/308

[58] Field of Search ..... 585/10, 12, 502, 709, 585/7; 526/308

[56] References Cited

U.S. PATENT DOCUMENTS

| | | | |
|---|---|---|---|
| 2,237,705 | 8/1943 | Frolich et al. | 585/12 |
| 2,732,408 | 1/1956 | Foote | 568/791 |
| 2,951,087 | 8/1960 | Hauser et al. | 502/62 |
| 3,173,965 | 3/1965 | Pappas et al. | 260/667 |
| 3,412,039 | 11/1968 | Miller | 252/428 |
| 3,432,571 | 3/1969 | Noddings et al. | 260/683.15 |
| 3,459,815 | 8/1969 | Noddings | 568/896 |
| 3,716,596 | 2/1973 | Bowes | 260/671 C |
| 3,845,150 | 9/1974 | Yan et al. | 260/673.5 |
| 3,849,507 | 11/1974 | Zuech | 260/671 |
| 3,876,720 | 4/1975 | Heilman et al. | 260/677 R |
| 3,959,399 | 5/1976 | Bridwell et al. | 260/671 C |
| 4,153,638 | 5/1979 | Bercik et al. | 585/526 |
| 4,214,111 | 7/1980 | Kitamura et al. | 585/255 |
| 4,299,730 | 11/1981 | Sommer et al. | 252/435 |
| 4,351,980 | 9/1982 | Reusser et al. | 585/820 |
| 4,380,509 | 4/1983 | Sommer et al. | 252/453 |

(List continued on next page.)

FOREIGN PATENT DOCUMENTS

| | | |
|---|---|---|
| 0036121 | 9/1981 | European Pat. Off. . |
| 0353813 | 2/1990 | European Pat. Off. . |
| 3668143 | 3/1971 | Germany . |
| 1489646 | 10/1957 | United Kingdom . |

OTHER PUBLICATIONS

Bolan: 'Synthetic Lubricant Base Stocks' Process Economics Program No. 125A by SRI International 4–3, pp. 239–249 (Dec. 1985).

Purnell, "Catalysis by Ion-Exchanged Montmorillonites," *Catalysis Letters*, 5 (1990) pp. 203–210.

Tsvetkov and Chagina, "Synthesis and Properties of Alkylnaphthalene Vacuum Pump Oil" All-Union Scientific Research Institute of Petroleum Processing, Neftepererabotka i Neftekhimiia, Moscow, (1) pp. 22–23.

Kuliev et al., "Preparation of High-Viscosity Synthetic Lubricants Using an Aluminosilicate Catalyst," Institute of Petrochemical Processes of the Academy of Sciences of the Azerbaidzhan SSR, Azerbaidzhanskoe, Neftiano. Khoziaistvo, 1983, No. 4, pp. 40–43.

Figueras, "Pillared Clays as Catalysts," *Catal. Rev.* -Sci. Eng., 30(3), pp. 457–499 (1988).

(List continued on next page.)

*Primary Examiner*—Shean Wu

*Attorney, Agent, or Firm*—James L. Bailey; Kenneth R. Priem; Russell R. Stolle

[57] ABSTRACT

Synthetic lubricant base stocks having improved properties are disclosed. The base stocks may be obtained by a two-step process, comprising the steps of (1) co-reacting vinylcyclohexene and long-chain linear olefin with a free-radical initiator; and (2) further reacting the mixture resulting from step (1) in the presence of an acidic montmorillonite clay.

9 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

U.S. PATENT DOCUMENTS

| | | | |
|---|---|---|---|
| 4,420,646 | 12/1983 | Darden et al. | 585/10 |
| 4,456,779 | 6/1984 | Owen et al. | 585/415 |
| 4,480,142 | 10/1984 | Cobb | 585/465 |
| 4,531,014 | 7/1985 | Gregory et al. | 585/435 |
| 4,556,750 | 12/1985 | Cobb | 585/446 |
| 4,604,491 | 8/1986 | Dressler et al. | 585/26 |
| 4,620,048 | 10/1986 | Ver Strate et al. | 585/10 |
| 4,788,362 | 11/1988 | Kaneko | 585/10 |
| 4,808,559 | 2/1989 | Sommer et al. | 502/63 |
| 4,827,064 | 5/1989 | Wu | 585/10 |
| 4,879,425 | 11/1989 | Kukes et al. | 585/350 |
| 4,892,680 | 1/1990 | Ishida | 252/565 |
| 4,962,262 | 10/1990 | Winter et al. | 585/512 |
| 4,967,029 | 10/1990 | Wu | 585/12 |
| 4,968,853 | 6/1990 | Scharf | 585/10 |

OTHER PUBLICATIONS

Friedlander, "Organized Polymerization. I. Olefins on a Clay Surface", Journal of Polymer Science: Part C, No. 4, pp. 1291–1301.

Friedlander et al., "Organized Polymerization III. Monomers Intercalated in Montmorillonite," Polymer Letters, vol. 2, pp. 475–479 (1964).

"Intercalated Catalysts and Pillared Clays," from a Process Evaluation/Research Planning Report by Chem Systems, titled Catalysts: Selected Developments 84–3, pp. 239–249 (Dec. 1985).

Bolan, "Synthetic Lubricant Base Stocks," Process Economics Program No. 125A by SRI International, Apr. 1989 & Supplement A. Sep. 1989.

"Synthetic Lubricants from Internal Olefins," Process Evaluation/Research Planning Report by Chem Systems, 84–Q–1, pp. 17–45.

Adams, "Synthetic Organic Chemistry Using Pillared, Cation–Exchanged and Acid–Treated Montmorillonite Catalysts—A Review", *Applied Clay Science,* 2 (1987) pp. 309–342.

Adams et al., "Clays as Selective Catalysts in Organic Synthesis," Journal of Inclusion Phenomena, vol. 5, (1987) pp. 663–674.

Chaudhuri & Sharma, "Some Novel Aspects of the Dimerization of a α–Methylstyrene with Acidic Ion–Exchange Resins Clays, and Other Acidic Materials as Catalysts," Ind–Eng. Res., vol. 28, pp. 1757–1763 (1989).

R. T. Sanderson, "Viscosity–Temperature Characteristics of Hydrocarbons" *Industrial and Engineering Chemistry,* vol. 41, No. 2 (Feb. 1949).

Dixon and Clark, "Physical Properties of High Molecular Weight Alkylbenzenes and Alkylcyclohexanes," *Journal of Chemical Engineering,* vol. 4, No. 1 (Jan. 1959).

SYNTHETIC LUBRICANT BASE STOCKS BY CO-REACTION OF VINYLCYCLOHEXENE AND LONG-CHAIN OLEFINS

CROSS-REFERENCE TO RELATED APPLICATIONS

This application is related to the following co-pending U.S. patent applications: Ser. No. 07/500,631, filed Mar. 28, 1990, which relates to the preparation of synthetic lubricant base stocks by oligomerizing linear olefins by means of certain acidic montmorillonite clays; Ser. No. 07/516,931, filed Apr. 30, 1990, which relates to the preparation of synthetic lubricant base stocks by oligomerizing certain mixtures of internal and alpha-olefins by means of certain acidic montmorillonite clays; Ser. No. 07/516,870, filed Apr. 30, 1990, which relates to synthetic lubricant base stocks made by oligomerizing linear olefins by means of certain aluminum nitrate-treated acidic montmorillonite clays; Ser. No. 07/522,941, filed May 14, 1990, which relates to the preparation of synthetic lubricant base stocks by co-oligomerizing propylene and long-chain alpha-olefins by means of certain acidic montmorillonite clay catalysts; Ser. No. 07/525,807, filed May 21, 1990, which concerns synthetic lubricant base stocks made by co-oligomerizing 1,3-di-isopropenyl benzene and long-chain alphaolefins by means of certain acidic montmorillonite clay catalysts; Ser. No. 07/531,172, filed May 31, 1990, which concerns synthetic lubricant base stocks having an improved pour point; Ser. No. 07/534,080, filed Jun. 6, 1990, which concerns synthetic lubricant base stocks having an improved viscosity; Ser. No. 07/536,906, filed Jun. 12, 1990, which concerns synthetic lubricant base stocks made by co-reacting olefins and anisole or like compounds; Ser. No. 07/545,260, filed Jun. 28, 1990, which concerns mixtures of oligomers and certain alkylated aromatics as synthetic lubricant base stocks; and Ser. No. 07/551,969, filed Jul. 12, 1990, which concerns a process for oligomerizing olefins using phosphorous-containing acid on montmorillonite clay. The totality of each of these previously filed applications is incorporated herein by reference.

BACKGROUND OF THE INVENTION

1. Field of the Invention

The invention relates to the preparation of synthetic lubricant base stocks, and more particularly to synthetic lubricant base stocks having improved properties, made by co-reacting vinylcyclohexene and long-chain olefins.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40–43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants discovered that it is possible to prepare synthetic lubricant base stocks in good yield by oligomerizing long-chain olefins using certain acidic montmorillonite clay catalysts. Applicants found that a high conversion of long-chain olefin to dimer, trimer, and tetramer may be obtained with formation of very little concomitant hydrogen redistribution by-product by using an acidic calcium montmorillonite clay having a moisture content ranging up to about 20 wt. %, a residual acidity in the range of about 3 to about 30 mg KOH/g (when titrated to a phenolphthalein end point), and a surface area of about 300 $M^2/g$ or greater. In addition to being excellent catalysts, these clays are non-hazardous and non-polluting.

With respect to the present invention, Applicants have found, surprisingly, that synthetic lubricant base stocks with a higher viscosity may be obtained where vinylcyclohexene and long-chain olefins are co-reacted. Additionally, incorporating the vinylcyclohexene lowers the cost of producing the base stocks by replacing a portion of the more expensive long-chain olefin feed with vinylcyclohexene. Applicants have discovered a two-step process for incorporating the vinylcyclohexene into the base stocks, comprising the steps of (1) co-reacting vinylcyclohexene and olefin with a free-radical initiator; and (2) reacting the mixture resulting from step (1) in the presence of an acidic montmorillonite clay.

SUMMARY OF THE INVENTION

The invention relates to a synthetic lubricant base stock, comprising a mixture of (1) oligomers prepared from a linear olefin having from 10 to 24 carbon atoms; and (2) a compound selected from the group consisting of the following formulas:

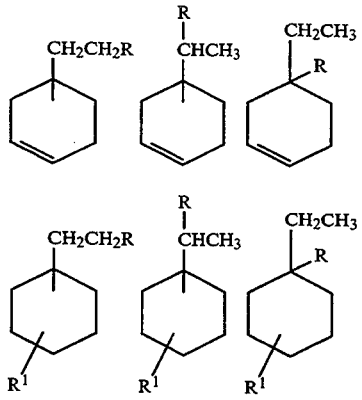

where R is an alkyl or alkenyl group having at least 10 carbon atoms and $R^1$ is an alkyl group having at least 10 carbon atoms. In another of its aspects, the invention relates to a synthetic lubricant base stock, comprising a mixture of (1) reduced oligomers prepared from a linear olefin having from 10 to 24 carbon atoms; and (2) a compound selected from the group consisting of the following formulas:

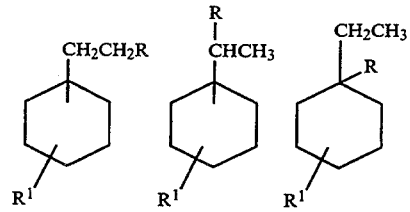

where R is an alkyl group having at least 10 carbon atoms and $R^1$ is H or an alkyl group having at least 10 carbon atoms. The invention further relates to a process for the preparation of synthetic lubricant base stocks, comprising the steps of (1) co-reacting vinylcyclohexene and a linear olefin having from 10 to 24 carbon atoms with a free-radical initiator; and (2) further reacting the mixture resulting from step (1) in the presence of an acidic montmorillonite clay.

DESCRIPTION OF THE PREFERRED EMBODIMENTS

Applicants have discovered that synthetic lubricant base stocks having improved properties may be prepared in good yield by co-reacting long-chain olefins and vinylcyclohexene using a two-step process, comprising the steps of (1) co-reacting vinylcyclohexene and a linear olefin having from 10 to 24 carbon atoms with a free-radical initiator; and (2) further reacting the mixture resulting from step (1) in the presence of an acidic montmorillonite clay. The resulting synthetic lubricant base stocks comprise a mixture of (1) oligomers of the $C_{10}$ to $C_{24}$ linear olefin; and (2) compounds selected from the group consisting of the following formulas:

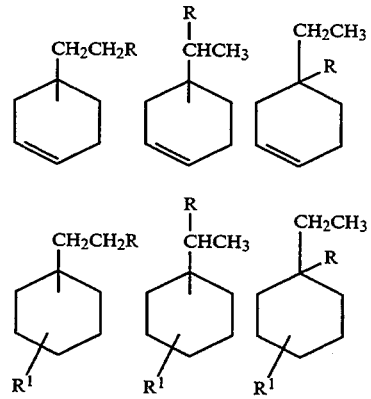

where R is an alkyl or alkenyl group having at least 10 carbon atoms and $R^1$ is an alkyl group having at least 10 carbon atoms. Preferably, the resulting mixture is then hydrogenated to reduce any unsaturation present in the oligomers, alkenyl groups and cyclohexene rings. Hydrogenation results in a synthetic lubricant base stock comprising a mixture of (1) reduced oligomers prepared from a linear olefin having from 10 to 24 carbon atoms;

and (2) a compound selected from the group consisting of the following formulas:

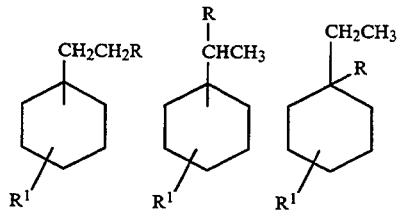

where R is an alkyl group having at least 10 carbon atoms and $R^1$ is H or an alkyl group having at least 10 carbon atoms.

Olefin monomer feed stocks useful in the present invention include compounds comprising (1) alpha-olefins having the formula $R''CH{=}CH_2$, where R'' is an alkyl radical of 8 to 22 carbon atoms, and (2) internal olefins having the formula $RCH{=}CHR'$, where R and R' are the same or different alkyl radicals of 1 to 21 carbon atoms, provided that the total number of carbon atoms in any one olefin shall be within the range of 10 to 24, inclusive. A preferred range for the total number of carbon atoms in any one olefin molecule is 14 to 18, inclusive. An especially preferred range is 14 to 16, inclusive. Mixtures of internal and alphaolefins may be used, as well as mixtures of olefins having different numbers of carbon atoms, provided that the total number of carbon atoms in any one olefin shall be within the range of 10 to 24, inclusive. The alpha and internal-olefins useful in the present invention may be obtained by processes well-known to those skilled in the art and are commercially available.

Vinylcyclohexene feedstocks may be obtained as a dimer of butadiene by processes well-known to those skilled in the art and are commercially available. As used herein, "vinylcyclohexene" is meant to include 4-vinyl-1-cyclohexene and its isomers, including compounds having the following formulas:

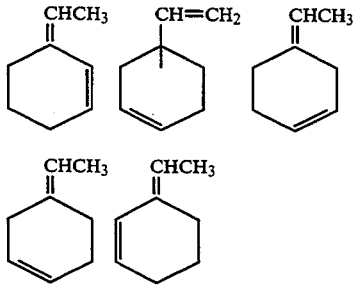

Preferably, the vinylcyclohexene comprises from about 1 to about 40 wt. % of the starting materials charged to the reactor (i.e. in a weight ratio of vinylcyclohexene to linear olefin of about 1:99 to about 2:3). It is especially preferred that the vinylcyclohexene comprise from about 5 to about 20 wt. % of the starting materials (i.e. in a weight ratio of vinylcyclohexene to linear olefin of about 1:20 to about 1:5).

In the first step, olefin and vinylcyclohexene are reacted with a free-radical initiator such as, for example, tert-butyl peroxybenzoate, di-tert-butyl peroxide, tert-butyl cumyl peroxide, benzoyl peroxide, acetyl peroxide, azo-bis(isobutyronitrile), and the like. Preferably, the free-radical initiator comprises from about 0.1 to about 10 wt. % of the reactor charge. Although Applicants' invention is not limited to any theory, it is believed that the free-radical initiator achieves some polymerization of the vinylcyclohexene, and results in a minor amount of olefin oligomerization. Surprisingly, as shown in the comparative examples, poor yields are obtained when the vinylcyclohexene and linear olefin are not first reacted with a free-radical initiator. Applicants believe this first step prevents the vinylcyclohexene from covering the active sites of the clay during the clay's catalysis of the reactions in the second step.

In the second step, the mixture of feedstocks, polymers and oligomers resulting from the first step is reacted in the presence of an acidic montmorillonite clay, resulting in a mixture comprising (1) oligomers of the $C_{10}$ to $C_{24}$ linear olefin; and (2) compounds selected from the group consisting of the following formulas:

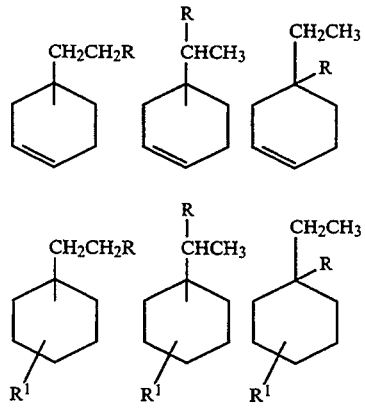

where R is an alkyl or alkenyl group having at least 10 carbon atoms and $R^1$ is an alkyl group having at least 10 carbon atoms.

The oligomerization of the linear olefin feedstock may be represented by the following general equation:

$$nC_mH_{2m} \xrightarrow{\text{catalyst}} C_{mn}H_{2mn}$$

where n represents moles of monomer and m represents the number of carbon atoms in the monomer. Thus, the oligomerization of 1-decene may be represented as follows:

$$nC_{10}H_{20} \xrightarrow{\text{catalyst}} C_{10n}H_{20n}$$

The oligomerization reactions occur sequentially. Initially, olefin monomer reacts with olefin monomer to form dimers. The dimers that are formed then react with additional olefin monomer to form trimers, and so on. This results in an oligomer product distribution that varies with reaction time. As the reaction time increases, the olefin monomer conversion increases, and the selectivities for the heavier oligomers increase.

The reaction of vinylcyclohexene and long-chain olefin, such as 1-decene, may result in several products. For example, the double bond of the vinyl group may react with decene, to form a higher molecular weight alkenyl group (via ionic reaction) or alkyl group (via free radical), as shown below:

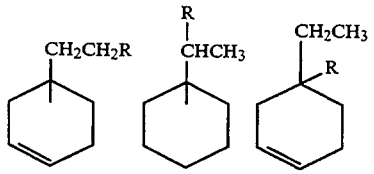

where R is an alkyl or alkenyl group having at least 10 carbon atoms. Depending on the mole ratio of linear olefin to vinylcyclohexene and reaction conditions, R may exceed 10 carbon atoms (in this case in multiples of 10) because after one molecule of decene reacts with the vinyl group to form an alkenyl group, another molecule of decene may react with the alkenyl group. Additionally, the double bond of the cyclohexene ring may react with decene to form an alkyl group. One or both double bonds also may react with other vinylcyclohexene.

The clay catalysts used in the present invention are certain silica-alumina clays, also called aluminosilicates. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

$$M_{x/n}\cdot^{n+}yH_2O(Al_{4-x}Mg_x)(Si_8)O_{20}(OH)_4$$

where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt. %, a residual acidity in the range of about 3 to about 30 mg KOH/g (when titrated to a phenolphthalein end point), and a surface area of about 300 $M^2/g$ or greater. Illustrative examples include Filtrol grade 24, having a moisture content of 12 wt. %, a residual acidity of 8.5 mg KOH/g, and a surface area of 425 $M^2/g$; Filtrol grade 124, having a moisture content of 2 wt. %, a residual acidity of 7.0 mg KOH/g, and a surface area of 400 $M^2/g$; Filtrol grade 13, having a moisture content of 16 wt. %, a residual acidity of 15 mg KOH/g, and a surface area of 300 $M^2/g$; Filtrol grade 113, having a moisture content of 4 wt. %, a residual acidity of 10 mg KOH/g, and a surface area of 300 $M^2/g$; and Filtrol grade 224, having virtually no moisture, and having a residual acidity of 3.0 mg KOH/g, and a surface area of 350 $M^2/g$.

Preferably, the catalyst is activated by heat treatment before running the reaction. Applicants have found that heat treatment of the catalyst prior to running the oligomerization reaction causes the catalyst to be more active and produce a higher olefin conversion. Additionally, clays heat-treated in this manner are more stable, remaining active during the oligomerization reaction for a longer period of time. The clays may be heat-treated at temperatures in the range of about 50° to 400° C., with or without the use of a vacuum. A more preferred temperature range is 50° to 300° C. Optionally, an inert gas may be used during heat treatment as well. Preferably, the clay should be heat-treated under conditions and for a length of time which will reduce the water content of the clay to approximately 1 wt. % or less.

The co-reactions of the present invention may be carried out in either a stirred slurry reactor or in a fixed bed continuous flow reactor. The catalyst concentration should be sufficient to provide the desired catalytic effect. The temperatures at which the reactions may be performed are between about 50° and 300° C., with the preferred range being about 150° to 180° C. The reaction may be run at pressures of from 0 to 1000 psig.

Following the reaction, it is preferred that the resulting mixture be hydrogenated to reduce any unsaturation present in the oligomers, alkenyl groups, and cyclohexene rings, to improve their thermal stability and to guard against oxidative degradation during the mixture's use as a lubricant. The hydrogenation reaction for 1-decene oligomers may be represented as follows:

$$C_{10n}H_{20n} + H_2 \xrightarrow{\text{catalyst}} C_{10n}H_{(20n+2)}$$

wherein n represents moles of monomer used to form the oligomer. Hydrogenation processes known to those skilled in the art may be used. A number of metal catalysts are suitable for promoting the hydrogenation reaction, including nickel, platinum, palladium, copper, and Raney nickel. These metals may be supported on a variety of porous materials such as kieselguhr, alumina, or charcoal. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

Unreacted monomer and vinylcyclohexene may be removed either prior to or after the hydrogenation step. Optionally, unreacted monomer and vinylcyclohexene may be stripped from the mixture prior to hydrogenation and recycled to the catalyst bed for co-reaction. The removal or recycle of unreacted monomer and vinylcyclohexene or, if after hydrogenation, the removal of non-oligomerized alkane and unreacted ethylcyclohexane, should be conducted under mild conditions using vacuum distillation procedures known to those skilled in the art. Distillation at temperature exceeding 250° C. may cause the oligomers to break down in some fashion and come off as volatiles. Preferably, therefore, the reboiler or pot temperature should be kept at or under about 180° C. Procedures known by those skilled in the art to be alternatives to vacuum distillation also may be employed to separate unreacted components from the mixture.

While it is known to include a distillation step after the hydrogenation procedure to obtain products of various 100° C. viscosities, it is preferred in the method of the present invention that no further distillation (beyond removal of any unreacted monomer/linear alkane and vinylcyclohexene/ethylcyclohexane) be conducted. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The invention will be further illustrated by the following examples, which are given by way of illustration and not as limitations on the scope of this invention. The entire text of every patent, patent application or other reference mentioned above is incorporated herein by reference.

EXAMPLES

Example 1

1-tetradecene (360 g), vinylcyclohexene (40 g), and tert-butyl peroxybenzoate (10 g) were charged to a liter flask equipped with a stirrer, a water cooled condenser, a heating mantle, a thermometer, and a nitrogen purge. The mixture was heated to 140° C. with stirring and held there for 5.0 hours. The mixture was cooled to ambient temperature, and 40 g of dry Harshaw/Filtrol Clay-13 was added. The reaction mixture was vigorously stirred, heated at 160° C. for 2.0 hours, and then at 180° C. for 3.0 hours. The mixture was cooled to ambient temperature, filtered with suction, and the effluent analyzed by liquid chromatography. The following results were obtained: 72.9% olefin conversion; 53.3% dimer; 18.1% trimer and higher oligomers. An unknown peak was observed between dimer and trimer and an unknown peak was observed between trimer and tetramer, indicating the incorporation of vinylcyclohexene into the oligomers. Neither peak is observed when 1-tetradecene is oligomerized in the absence of vinylcyclohexene. There was no indication of unreacted vinylcyclohexene.

The liquid effluent from this reaction was charged to a liter autoclave with 5% nickel catalyst. The autoclave was then sealed, flushed with hydrogen, pressured to 1000 psig with hydrogen and heated to 200° C. The mixture was heated at 200° C. for 4.0 hours with vigorous stirring. Hydrogen was added as needed to maintain the pressure at 2000 psig. The mixture was cooled to ambient temperature, vented, and the catalyst removed by filtration. The unreacted monomer was removed by vacuum distillation to a pot temperature of 215° C. and a head temperature of >150° C. (1.0 mm Hg) to give a synthetic lubricant with the following properties: 210° F. viscosity=6.98 cSt; viscosity index=125; cold crank simulation=1800 cp; pour point=−20° F.; and Noack (250° C. )=14.1%.

Example 2

The same procedure was used as in Example 1 above, except that 8.0 g of tert-butyl peroxybenzoate was used in the first step and the reaction mixture was held at 140° C. for 6.0 hours. In the second step, the reaction mixture was heated with 40 g dry Harshaw/Filtrol Clay-13 for 3.0 hours at 160° C. and then for 2.0 hours at 180° C. Workup as above showed 67.6% olefin conversion, 55.4% dimer, and 10.8% trimer and higher oligomers. There was only a small amount of unreacted vinylcyclohexene present.

The liquid reactor effluent from this reaction was reduced and the monomer flashed as in Example 1 to give a synthetic lubricant with the following properties: 210° F. viscosity=6.80 cSt; viscosity index=123; cold crank simulation=1500 cp; and Noack (250° C.)=18.0%.

Example 3

The same procedure was used as in Example 1 above, except that the 1-tetradecene was replaced by 1-hexadecene. The mixture was heated at 140° C. for 6.0 hours. The mixture was then cooled to ambient temperature, and 40 g dry H/F Clay-13 was added. The mixture was heated (with vigorous stirring) at 160° C. for 3.0 hours and then at 180° C. for 2.0 hours. The mixture was filtered with suction, and the effluent analyzed by liquid chromatography, which showed 64.3% olefin conversion, 46.6% dimer, and 7.99% trimer and higher oligomers.

The liquid reactor effluent from this reaction was reduced and the monomer flashed as in Example 1 to give a synthetic lubricant with the following properties: 210° F. viscosity=8.66 cSt; viscosity index=126; cold crank simulation=4150 cp; and Noack (250° C.)=8.72%.

Example 4

The same procedure was used as in Example 1 above, except that 8.0 g of tert-butyl peroxybenzoate was used and the mixture was heated for 4.0 hours at 130° C. The mixture was then cooled to ambient temperature and 40 g of dry H/F Clay-24 was added. After stirring the mixture at 160° C. for 5.0 hours, it was cooled to ambient temperature and filtered. The effluent was analyzed by liquid chromatography and showed 50.4% olefin conversion, 33.4% dimer, and 14.9% trimer and higher oligomers.

The liquid reactor effluent from this reaction was reduced and the monomer flashed as in Example 1 to give a synthetic lubricant with the following properties: 210° F. viscosity 7.50 cSt; viscosity index=122; cold crank simulation=2050 cp; and Noack (250° C.)=17.5%.

Comparative Example 1

1-tetradecene (300 g), vinylcyclohexene (100 g), and dry Harshaw/Filtrol Clay-24 (40 g) were charged to an autoclave. The autoclave was sealed and heated to 160° C. The mixture was then heated for four hours at 160° C. with vigorous stirring. The mixture was cooled to ambient temperature, filtered with suction, and the liquid product analyzed by liquid chromatography. The only product formed in a significant amount was dimer (8.11%). There was no evidence of incorporation of vinylcyclohexene into oligomers.

Comparative Example 2

1-tetradecene (200 g), vinylcyclohexene (200 g), and dry Harshaw/Filtrol Clay-24 (40 g) were charged to an autoclave. The autoclave was sealed and heated to 160° C. The mixture was then heated for four hours at 160° C. with vigorous stirring. The mixture was cooled to ambient temperature, filtered with suction, and the product analyzed by liquid chromatography. There was no dimer or oligomer formed in significant yield.

We claim:

1. A synthetic lubricant base stock, comprising a mixture of (1) oligomers prepared from linear olefins having from 10 to 24 carbon atoms; and (2) a compound selected from the group consisting of compounds having the following formulas:

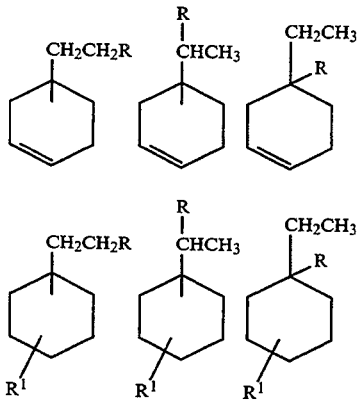

where R is an alkyl or alkenyl group having at least 10 carbon atoms and $R^1$ is an alkyl group having at least 10 carbon atoms, wherein said mixture is a liquid at room temperature.

2. The synthetic lubricant base stock of claim 1, wherein the oligomers are prepared from linear olefins having from 14 to 18 carbon atoms, R is an alkyl or alkenyl group having at least 14 carbon atoms, and $R^1$ is an alkyl group having at least 14 carbon atoms.

3. The synthetic lubricant base stock of claim 1, wherein the mixture comprises co-reaction products of linear olefins having from 10 to 24 carbon atoms and vinylcyclohexene.

4. The synthetic lubricant base stock of claim 1, wherein the double bonds of the oligomers have been reduced by catalytic hydrogenation and R is an alkyl group having at least 10 carbon atoms.

5. The synthetic lubricant base stock of claim 1, wherein the mixture comprises co-reaction products of linear olefins having from 14 to 18 carbon atoms and vinylcyclohexene, and wherein the double bonds of the oligomers have been reduced by catalytic hydrogenation and R is an alkyl group having at least 14 carbon atoms.

6. A synthetic lubricant base stock, comprising a mixture of (1) reduced oligomers prepared from linear olefins having from 10 to 24 carbon atoms; and (2) a compound selected from the group consisting of compounds having the following formulas:

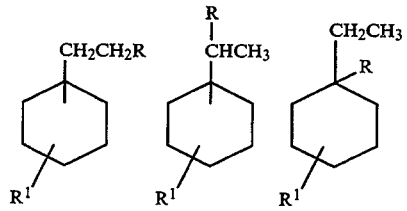

where R is an alkyl group having at least 10 carbon atoms and $R^1$ is an alkyl group having at least 10 carbon atoms, wherein said mixture is a liquid at room temperature.

7. The synthetic lubricant base stock of claim 6, wherein the reduced oligomers and catalytically hydrogenated oligomers prepared from linear olefins having from 14 to 18 carbon atoms, R is an alkyl group having at least 14 carbon atoms, and $R^1$ is an alkyl group having at least 14 carbon atoms.

8. The synthetic lubricant base stock of claim 6, wherein the mixture comprises hydrogenated co-reaction products of linear olefins having from 10 to 24 carbon atoms and vinylcyclohexene.

9. The synthetic lubricant base stock of claim 6, wherein the mixture comprises hydrogenated co-reaction products of linear olefins having from 14 to 18 carbon atoms and vinylcyclohexene; R is an alkyl group having at least 14 carbon atoms; and $R^1$ is an alkyl group having at least 14 carbon atoms.

* * * * *